United States Patent [19]
Kozulic et al.

[11] Patent Number: 5,319,046
[45] Date of Patent: Jun. 7, 1994

[54] POLYMERS, AND THEIR USE AS GELS FOR ELECTROPHORESIS

[75] Inventors: Branko Kozulic, Zürich; Klaus Mosbach, Oberengstrigen, both of Switzerland

[73] Assignee: Elchrom, Ltd., Horgen, Switzerland

[21] Appl. No.: 328,123

[22] PCT Filed: Jun. 10, 1988

[86] PCT No.: PCT/EP88/00515

§ 371 Date: Jan. 31, 1989

§ 102(e) Date: Jan. 31, 1989

[87] PCT Pub. No.: WO88/09981

PCT Pub. Date: Dec. 15, 1988

[30] Foreign Application Priority Data

Jun. 13, 1987 [GB] United Kingdom ............... 8713854

[51] Int. Cl.$^5$ ................... C08F 20/54; C08L 89/00
[52] U.S. Cl. ..................... 526/304; 526/312; 526/310; 524/704; 524/916; 525/54.1; 525/329.4; 204/182.6
[58] Field of Search ............... 526/312, 304; 524/704, 524/916; 525/54.1, 329.4; 204/182.6

[56] References Cited

U.S. PATENT DOCUMENTS

| | | | |
|---|---|---|---|
| 4,192,784 | 3/1980 | Brown et al. | 360/8 |
| 4,452,916 | 6/1984 | Boschetti | 521/38 |
| 4,806,434 | 2/1989 | Ogawa | 524/916 |

FOREIGN PATENT DOCUMENTS

| | | |
|---|---|---|
| 0040124 | 11/1981 | European Pat. Off. . |
| 2359873 | 2/1978 | France . |

OTHER PUBLICATIONS

Jedinski, Z., et al; J. Polym. Sci., 5 (1967), 2957–60.
Girot, P., et al; J. Chromatog. 213 (1981), 389–96.
Mirjana Kozulic et al; Analytical Biochemistry; Poly-N-acryloyl-Tris Gels as Anticonvection Media for Electrophoresis and Isoelectric Focusing; Copyright 1987; pp. 506–512.
Righeti et al., "Isoelectric Focusing and Non-Isoelectric Precipitation of Ferritin In Immobilized pH Gradients: An Improved Protocol Overcoming Protein-Matrix Interactions", *Electrophoresis* (1987) 8, 62–70.
Righeti, "Of Matrices and Men", *Journal of Biochemical and Biophysical Methods* (1989) 19, 1–20.
Boschetti, "Polyacrylamide Derivatives To The Service of Bioseparations", *Journal of Biochemical and Biophysical Methods* (1989) 19, 21–36.

Primary Examiner—Paul R. Michl
Assistant Examiner—Tae H. Yoon
Attorney, Agent, or Firm—Nikaido, Marmelstein, Murray & Oram

[57] ABSTRACT

A novel synthesis of N-acryloyl-tris-(hydroxymethyl)aminomethane (NAT) is described. The polymerization kinetics and transparency of the poly(NAT) gels crosslinked by a crosslinker (CL) e.g. N,N'-methylenebisacrylamide (Bis), i.e. poly(NAT+Bis) polymer, are shown. Poly(NAT+Bis) gradient (4–24%) gels were prepared and found to resolve native proteins according to their size. The exclusion limit of these gels is over $3 \times 10^6$ Da. This is more than threefold higher than the exclusion limit of the polyacrylamide gradient gel of the same concentration. Therefore poly(NAT+CL) gels are better than polyacrylamide gels for the resolution of large proteins. It was demonstrated that poly(NAT+CL)-polyacrylamide composite gels could be prepared. The poly(NAT+CL) gels were found to be advantageous also for isoelectric focussing in carrier ampholytes or immobilized pH gradients. Poly(NAT+CL) gels are also very good for separation of nucleic acids. The resolution is particularly good in the range between several hundred to 4–5000 base pairs. Under the optimized conditions, DNA molecules of more than 20 kbases can be perfectly resolved.

34 Claims, 3 Drawing Sheets

POLYMERS, AND THEIR USE AS GELS FOR ELECTROPHORESIS

FIELD OF INVENTION

This invention concerns polymers, and their use as gels for electrophoresis.

BACKGROUND TO THE INVENTION

Electrophoresis is a technique in which molecules or other units move along a support medium under the influence of an electric field. Because different kinds of molecules and units behave differently, with migration rates depending on charge and frictional resistance, the technique is widely used for separation purposes. Commonly the support medium is a gel, and is used as in the form of a flat sheet; the mixture to be separated is placed at one end of the sheet; and a suitable electric field is applied along the sheet (from one end to the other) causing differential migration of the molecules or units in the mixture, resulting in separation.

Electrophoresis may be applied for many purposes, and is typically used for the separation of mixtures of biomolecules, that is molecules found in living organisms. These are typified by cell proteins and nucleic acids e.g. DNA (deoxyribonucleic acid) and fragments or denatured versions thereof, as well as many polysaccharides, polyphosphates, and proteoglycans.

It is naturally important that the gel itself should not be affected by the electric field The most widely used anticonvective media for electrophoretic separations of bio-molecules are based on acrylamide polymers or agarose. Both of these are hydrophilic relatively stable polymers carrying practically no charge (polyacrylamide) or only a small number of charged groups (agarose) (see Johansson, B. G., Hjerten, S. (1974) Anal. Biochem. 59, 200–213.

The known acrylamide polymer gels are acrylamide crosslinked by N,N'-methylenebisacrylamide (Bis). They are referred to hereinafter as poly(acrylamide+-Bis), and are excellent for the separation of molecules with molecular masses from 2 to 5 up to 1000 kDa, whether under denaturing or nondenaturing conditions (see Bothe, D., Simonis, M., and Dohren, H. V., (1985) Anal. Biochem. 151, 49–54; Campbell, W. P., Wrigley, C. M., and Margolis, J., (1983) Anal. Biochem. 129, 31–36; and Lambin, P., (1978) Anal. Biochem. 85, 114–125. Larger molecules or multimolecular complexes, however, cannot be satisfactorily resolved, due to the pronounced sieving effect of the poly(acrylamide+Bis) gels even of the lowest workable concentration (approximately 3%). On the other hand, the more porous agarose gels are not suitable in some applications (see Bosisio, A. B., Loeherlein, C, Snyder, R. S., and Righetti, P. G., (1980) J. Chromatogr. 189, 317–330; and Righetti, P. G., (1986) Sci. Tools 33, 1–4, mostly because endo-osmosis, caused by the residual charged groups in the matrix, impairs resolution.

There have been numerous attempts to produce more porous polyacrylamide gels by increasing the concentration of Bis above 5% Rodbard, D., Levitov, C. and Chrambach, A. (1972), Sep. Sci. 7, 705–723; and Chrambach, A., and Rodbard, D., (1971) Science, 172, 440–451 or by using a new cross-linker Baumann, G., and Chrambach, A., (1976) Anal. Biochem. 70, 32–38. Moreover, composite polyacrylamide-agarose gels have also been tested as media for electrophoresis Bode, H. J. (1977) Anal. Biochem. 83, 204–210 and 364–371, and Pino, R. M. and Hart, T. K. (1984) Anal. Biochem. 139, 77–81.

In addition to electrophoretic analysis of large biomolecules, highly porous matrices would be beneficial for other electrophoretic techniques where the extensive sieving of poly(acrylamide+Bis) gels represents a drawback. These include isoelectric focussing (IEF) in carrier ampholytes or in immobilised pH gradients (IPG) Righetti, P. G., (1983) in Isoelectric Focusing: Theory, Methodology, and Applications (Work, T. S. and Burdon, R. H. Eds.). Elsevier, Amsterdam and New York, as well as in titration curves Bosisio, A. B., Loeherlein, C, Snyder, R. S., and Righetti, P. G., (1980) J. Chromatogr. 189, 317–330. Furthermore, nonsieving media are required for stacking gels in multiphasic zone electrophoresis Jovin, T. M. (1973) Biochemistry, 12, 871–898, and Wyckoff, M., and Rodbard, D., and Chrambach, A., (1977), Anal. Biochem. 78, 459–482.

The present invention aims to provide novel polymers for use as gels suitable for use in electrophoresis.

SUMMARY OF THE INVENTION

According to one aspect of the invention, there is provided a polymer comprising N-acryloyl-tris(hydroxymethyl)aminomethane (NAT) crosslinked by a cross linker (CL) containing two or more double bonds. This polymer may for convenience be referred to as poly(-NAT+CL).

Although crosslinkers such as N, N'-(1,2-dihydroxyethylene)bisacrylamide, N,N'-bis-acrylylcystamine, and ethylene diacrylate, may be employed, the preferred cross-linker comprises N,N'-methylenebisacrylamide (Bis). In that event, the polymer may conveniently be referred to as poly(NAT+Bis).

The poly(NAT+CL) of the invention may be prepared in essence simply by reacting NAT with the cross-linker. NAT and Bis possess acrylic-type double bonds, and it is well known that polymerisation of acrylic monomers can be effected in various ways, e.g. by heat, gamma radiation, reaction with free radicals, etc. Depending on polymerisation conditions, such as concentrations of NAT and CL, temperature, various solvents and initiators, the cross-linked polymers formed may be gel-like or may have properties different from those of a gel.

The formed poly(NAT+CL) can be obtained in a range of physical states. One state of particular interest is as a gel, that is, a solid dispersion of water in the polymer. These gels are of great value as a support medium for electrophoresis.

In a further aspect, therefore, the invention provides a gel for use in electrophoresis comprising poly(-NAT+CL).

The cross linker CL is preferably Bis.

The gel desirably comprises between 4 and 24% (T) poly (NAT+CL), of which 5% (C) or less is Bis, because such gels are more transparent.

The gel concentration (T) and the amount of cross linker (C) are defined as follows. Total gel concentration (T) is the sum of monomer and the cross-linker weights (that is to say, the total solids making up the polymer), expressed in grams per 100 ml of solution. Concentration of the cross-linker (C) is given as the percentage weight of the cross-linker in relation to the sum of the monomer and cross-linker weights. Thus, for example, 5% T, 3% C would contain 4.850 g of NAT and 0.150 g of CL in 100 ml of solution. In gels with small C, the difference between monomer concentration and T is very small, and it is sometimes neglected in discussion.

The gel may be homogenous (i.e. with uniform T throughout), or it may be in the form of a gradient gel, e.g. having a poly(NAT+CL) content ranging from 4% to 24% (T) along the length of a sheet of the gel.

The gel may also be mixed with a further polymeric material such as polyacrylamide or agarose or it may incorporate an additional monomer. Such a composite gel is conveniently in the form of a gradient gel, having a composition at one end of 4% (T) that is solely poly(-NAT+CL) and at the other end of 24% (T) that is solely poly(acrylamide+CL). Such a gel may advantageously be prepared by co-polymerising the NAT with the further gel material e.g. acrylamide and the cross linker.

Gels in accordance with the invention are found to perform well as a medium for electrophoretic separation and isoelectric focussing. The 4 to 24% poly(-NAT+CL) gradient gels resolve native proteins according to size. The exclusion limit of these gradient gels was found to be over $3 \times 10^6$ Da, which is more than three times the exclusion limit of polyacrylamide gradient gels of the same concentration. Thus such poly(NAT+CL) gels are better than comparable polyacrylamide gels for the resolution of large native proteins. Results also show that the poly(NAT+CL)-Bis gels can advantageously be used in applications where the extensive sieving by a polyacrylamide matrix is not desirable.

Poly(NAT+CL) gels are also very good for the separation of nucleic acids. The resolution is particularly good for acids with between one or two hundred and 4000 to 5000 base pairs. Under optimised conditions, DNA molecules of more than 20k bases can be perfectly resolved (reference 28).

The term "nucleic acids" as used herein is intended to include both small and large molecules (oligonucleotides and polynucleotides) and fragments thereof. One of the most interesting applications of poly(NAT+CL) gels might be for analysis of DNA sequences. The sizes of DNA fragments which need to be resolved are in the range from a few tens to a few hundreds of nucleotides, which is well within the optimal separation range of poly(NAT+Bis) gels Kozulic, B., Mosback, K., and Pietrzak, M. (1988), Anal. Biochem. 170, 478–484.

In addition, poly(NAT+CL) gels have excellent drying and swelling properties: i.e., they do not crack upon drying, and on re-wetting they swell to the original size in a short time.

In a further aspect the present invention also provides a method of electrophoresis, in which the electrophoresis is effected using as the support medium a poly(-NAT+CL) gel in accordance with the invention.

The method of the invention can be used for resolving a wide range of materials including native proteins, denatured proteins, nucleic acids, denatured nucleic acids, other molecules having intrinsic charged groups (e.g. polysacharides, polyphosphates, proteoglycanes, synthetic polymers etc), and molecules with charges formed by derivatization of uncharged molecules.

Electrophoresis can be performed with or without discontinuities in time or electric field, on a homogenous gel with continuous or discontinuous buffer systems or in a gradient gel.

The invention can also be applied to isoelectric focussing, in a pH gradient formed by carrier ampholytes or in an immobilised pH gradient.

The N-acryloyl-tris(hydroxymethyl)aminomethane, or NAT, used to make the poly(NAT+CL) of the invention is a known compound, and can be prepared in any one of the known ways, e.g. by the reaction of acryloyl chloride with tris(hydroxymethyl)aminomethane. We have found however, that careful control of the reaction and the subsequent separation and purification of the final product gives a better quality NAT.

In yet a further aspect, therefore, the invention provides a process for the preparation of N-acryloyl-tris(-hydroxymethyl)aminomethane (NAT) by the reaction of acryloyl chloride with tris(hydroxymethyl)aminomethane (Tris), in which the reaction is effected in the presence of a strong base and in a two phase aqueous organic solvent medium to give a desired NAT product in the aqueous phase, and this phase is isolated, purified by an ion-exchange method using a mixture of strong cationic and weak anionic ion exchange resins, and evaporated at atmospheric pressure to give the desired NAT.

The strong base is preferably an alkali metal hydroxide, typically potassium hydroxide, and the reaction is conveniently effected at a pH of from 8 to 9. Moreover, advantageously the reaction is carried out with cooling, to at or near 0° C., and in the presence of a polymerisation inhibitor such as sodium nitrite.

The aqueous organic two phase medium is preferably an aqueous halocarbon, typically aqueous dichloromethane.

The isolated aqueous phase, containing the prepared NAT, is advantageously purified using a mixture of a strong cationic ion-exchange resin (IR-120, H+ form) and a weak anionic ion-exchange resin (IRA-68, free base form)

The invention also extends the N-acryloyl-tris(hydroxymethyl)aminomethane, whenever prepared by the above defined process.

The invention will further be described, by way of illustration, by reference to the accompanying drawings in which.

SYNTHESIS OF NAT

The Tris, acryloyl chloride, and other chemicals for synthesis were from Fluka.

Tris (60.5 g, 0.5 mol) was dissolved in 120 ml of water. Into this solution 3 g $K_2CO_3$ and 3.5 g of $NaNO_2$ (polymerization inhibitor) were added, and the solution was cooled in an ice bath. Approximately 100 ml of dichloromethane was poured in and the mixture was vigorously stirred with a magnetic stirrer in a fume cupboard.

KOH (40 g) was dissolved in 50 ml of water and cooled. Freshly distilled acryloyl chloride (50 g, 0.55 mol) was mixed with 50 ml of dichloromethane. Approximately one third of this solution was added in portions to the stirred suspension within 15 min, followed by the alternate additions (in 1- to 2-ml aliquots) of potassium hydroxide and acryloyl chloride solutions. The pH was monitored by a narrow-range pH paper, and kept between 8 and 9. After all of the acryloyl chloride had been added, the suspension was vigorously stirred for half an hour in an ice bath, with the pH being kept slightly alkaline.

The phases were then separated and the lower, organic phase was discarded. Four volumes of absolute ethanol were added to the water phase while cooling in the ice bath. The precipitated salts were removed by filtration. Portions of a strong cationic ion exchanger (IR-120, $H^+$ form) and of a weak anionic exchanger (IRA-68, free base) were added to the stirred filtrate until the reaction for chloride was negative. The mixed ion exchangers were removed and washed on a funnel or in a wide column. The combined washings and the filtrate were poured into crystallisation dishes ($30 \times 18$ cm), and left in the fume cupboard The solvents evaporated within 3-5 days. The crystals were collected on the sinter funnel, and washed with cold ethanol. The yield was 48 g or 55% and the crystals were stored at $+4°$ C.

If the formed NAT needs to be stored for long periods, small amounts (0.01-0.1%, w/w) of p-methoxy phenol should be added to the NAT solution after treatment with the mixed ion exchangers. In preparations without p-methoxy phenol, it is noticeable that much more insoluble polymers occur after one year than in the preparations with this added polymerisation inhibitor.

Although NAT thus obtained is sufficiently pure for most applications, further purification, if necessary, can be achieved by recrystallization from acetonitrile (reference 18).

NAT tends to polymerize spontaneously during the synthesis and workup when polymerization inhibitors are not present or the temperature rises above 40°-50° C. Even in the presence of an inhibitor (p-methoxyphenol) and low temperatures (30°-35° C.), various amounts of insoluble polymers were always present when evaporation of the desalted solution was done on a rotary evaporator. These polymers could be removed by filtration, but it was better when water evaporated from the crystallization dishes (see above) since the quantity of the insoluble polymers formed was then negligible. The inhibitor (p-methoxyphenol) must be added before crystallization is attempted from acetonitrile. Precipitation of salts by ethanol could be omitted, but much larger quantities of the ion exchangers are then needed and the yield is decreased. Substitution of the strong anionic ion exchanger (IRA-400, hydroxide form) for the weak one (IRA-68) also lowered the yield. The mixed ion exchangers can be easily recovered from the saturated sodium chloride solution for regeneration and reuse.

POLYMERISATION OF NAT+CL (BIS)

NAT and Bis possess acrylic-type double bonds, and it is well known that polymerisation of acrylic monomers can be effected in various ways, eg by heat, gamma radiation, reaction with free radicals, etc. Depending on polymerisation conditions, such as concentrations of NAT and CL, temperature, various solvents and initiators, the cross-linked polymers formed may be gel-like or may have properties different from those of a gel.

PRODUCTION OF GELS FOR ELECTROPHORESIS

All materials for electrophoresis were from Bio-Rad. Electrophoresis was performed in a Pharmacia electrophoresis apparatus.

Gradient gels (4-24% T, 2.6% C) were prepared in cassettes ($80 \times 80 \times 0.7$ mm) in a V-shaped casting apparatus according to instructions in the Pharmacia Polyacrylamide Gel Electrophoresis Manual.

To prepare four poly(NAT+Bis) gels, the following solutions were made. NAT (3.506 g) and Bis (0.094 g) were dissolved in 15 ml of 0.1M Tris-HCl, pH 9 under slight heating, if necessary. (NAT dissolves better in pure water than in Tris buffers, and sometimes it is preferential to dissolve it first in water and then dilute to the desired concentration with a concentrated Tris buffer.) Next, 3.5 ml of this (24%) solution were diluted with the Tris buffer to 21 ml, to make the 4% solution. These solutions, as well as the casting apparatus with cassettes, were cooled to around $+4°$ C. (in a cold room: NAT tends to crystallise from the cold 24% solution, and therefore the cooled solution should be used quickly). A volume of 0.058 ml of N,N,N',N'-tetramethylethylenediamine (TEMED, the catalyst) and 0.770 ml of ammonium persulfate (the initiator) solution (15 mg/ml of water) were added to 21 ml of the 4& (NAT+Bis) solution. After brief mixing, 10 ml of this solution was immediately pumped into the casting apparatus. Then, 11 ml of the same solution was placed in one chamber of the gradient mixer (purchased from Kontron), and the stirrer was inserted. To the 24% solution, 0.017 ml of TEMED and 0.290 ml of ammonium persulfate (15 mg/ml) were added, mixed, and 11 ml of this solution was placed in another chamber of the gradient mixer. The stirrer and the pump (Gilson, minipuls) were started, and a tube between the two chambers was opened. After the contents of both chambers had been pumped in the casting apparatus, 40% (w/v) sucrose solution (in the Tris buff®r) was placed in the first chamber and pumped in the casting apparatus to displace the gradient into the cassettes. The pumping was stopped when the sucrose front reached the bottom of the cassettes. Then, the tubing between the casting apparatus and the pump was closed with a clamp, released from the pump and fixed to the casting apparatus in such a way that its open end remained above the level of the (NAT +Bis) solution in the casting apparatus. The casting apparatus was then carefully taken out of the cold room, the clamp opened (disturbances in the gradient were occasionally observed when the system was not opened during polymerisation) and the gel left undisturbed to polymerise for at least 2 hours or preferentially longer (overnight). Poly(NAT+Bis) gels should not be stored refrigerated (at +4° C.), as such gels do not adhere well to the glass plates.

Gels for isoelectric focussing (120×80×1 mm), composed of NAT and Bis (T=6%, C=3%) were cast by capillarity. Freshly made monomer solutions were usually treated with mixed ion exchangers, and filtered through a 0.45-um membrane filter. The combination of a strong cationic (Dowex 50, H+) and a weak anionic (IRA 68, free base) exchanger packed (each in three segments) in the Pharmacia PD-10 column was found superior to the AG 501X8(D) mixed ion exchangers (Bio-Rad). For 10 ml solution NAT and Bis in water, 0.020 ml of TEMED and 0.250 ml of ammonium persulphate (15 mg/ml) were used.

Gels were polymerized on the plastic sheet (Gel Bond) and the glass plate used was made hydrophobic by silanization in order to facilitate its removal after polymerization.

The gel fixed to the plastic sheet was weighed and washed with distilled water (twice for 15 min). It was then dried by standing overnight at room temperature (at this stage it can be stored at +4° C. for at least 1 week) and weighed again. Ampholines (final concentration 2% by wt) were then mixed with the volume (ml) of water equal to the lost weight (g), and introduced above the gel in the same manner as used when it was cast. Swelling of the gel was usually completed in 2 hours and it could immediately be used for isoelectric focussing (IEF).

POLYMERISATION KINETICS AND GEL TESTING

The polymerization kinetics of the NAT and acrylamide monomer solutions of the same molar concentration were analysed by monitoring the decrease of absorbancy in the near UV Gelfi, C. and Righetti, P. G. (1981), Electrophoresis, 2, 213-219, which is proportional to the disappearance of acrylic double bonds.

Figure 1A:
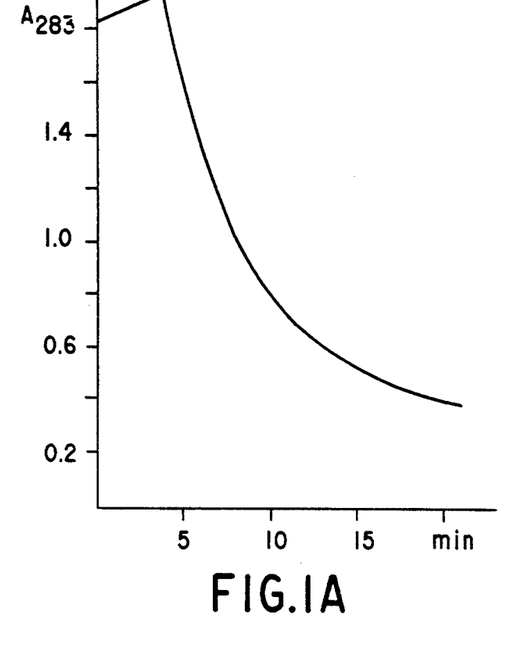
FIGS. 1A and 1B are graphs illustrating polymerisation kinetics of monomers comprising 5% by wt (0.7M) acrylamide (A) and 12.5% by wt (0.7M) NAT (B)
Figure 1B:
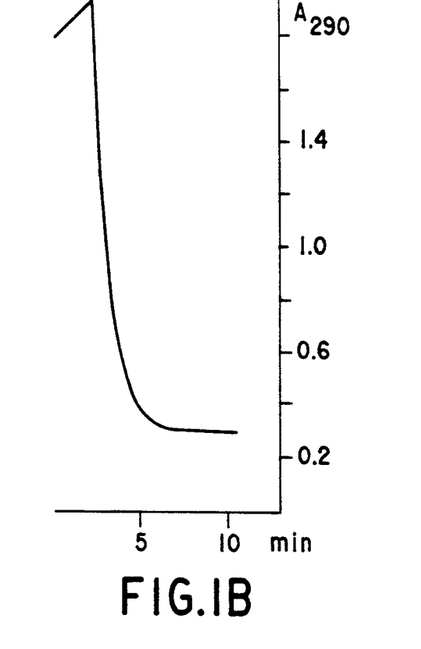

Tests were carried out by adding to a 1-ml solution of the monomers in 0.1M Tris-HCl buffer, pH 9.0, in a quartz cuvette, TEMED (6 ul, 25%) and ammonium persulphate (35 ul, 15 mg/ml). The solution was quickly mixed and overlid with diisopropylether. The wavelengths giving starting absorbancy of 1.8 against the buffer were selected. The results are shown in FIG. 1.

Under the conditions applied, polymerisation is characterised by an incubation period lasting 2-5 min, followed by the rapid conversion of monomers into the growing polymer chains. Most of the acrylamide (FIG. 1A) and all of the NAT (FIG. 1B) are polymerised within 10 min. The conversion yield, estimated from the ratio of absorbancy at the beginning and at the end of polymerization Gelfi, C. and Righetti, P. G. (1981), Electrophoresis, 2, 213-219, appears to be quite similar.

Gels formed with a low amount of the crosslinker are transparent, but it is well known that poly(acrylamide+Bis) gels with high Bis concentrations become opaque Rodbard, D., Levitov, C. and Chrambach, A. (1972), Sep. Sci. 7, 705-723; and Chrambach, A. In acrylamide-Bis mixtures it was found Campbell, W. P., Wrigley, C. M., and Margolis, J., (1983) Anal. Biochem. 129, 31-36 that the onset of opacity depends not only on Bis but also on the total monomer concentration. Thus, higher amounts of the crosslinker still produced transparent gels when the total monomer concentration was increased (reference 3).

Figure 2:
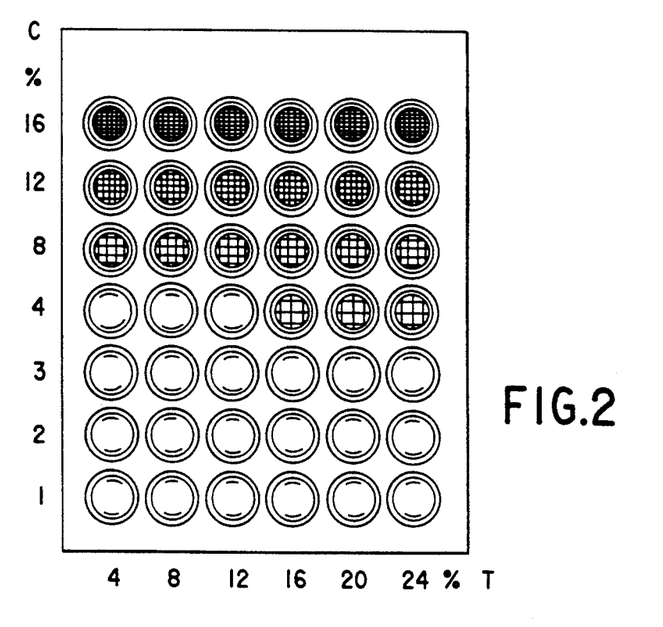
FIG. 2 illustrates the transparency of poly(NAT+-Bis) gels at various total monomer (T) and crosslinker (C) concentrations.

42 different NAT-Bis combinations, were polymerised, starting with 4% (T) NAT and 1% (C) Bis, and ending with 24% (T) NAT and 16% (C) Bis, to check the transparency of these gels. The results are shown in FIG. 2.

All gels crosslinked with less than 3% Bis were transparent. Two gels of the lower total monomer concentration (4% and 8%) containing 4% Bis were still transparent, but all other more crosslinked gels became turbid. It was not possible to test whether more concentrated (above 24%) poly(NAT+Bis) gels could be made with more Bis before turning opaque, as found for poly(acrylamide+Bis) (reference 3), because the saturated solution of NAT at room temperature is approximately 24%. Transparency of the two 4% crosslinked gels is somewhat unexpected, but two additional independent polymerizations gave the same result.

ELECTROPHORESIS TEST RESULTS

Sieving properties of the poly(NAT+Bis) gel were tested by preparing a 4% to 24% gradient gel and comparing the migration of proteins in this and in an a poly(acrylamide+Bis) gradient gel of the same concentration. Electrophoresis in poly(acrylamide+Bis) gradient gels resolves native proteins according to their size Lambin, P., (1978) Anal. Biochem. 85, 114-125; and Rothe, G. M., and Purkhanbaba, H. (1982) Electrophoresis, 3, 33-42.

Figure 3:
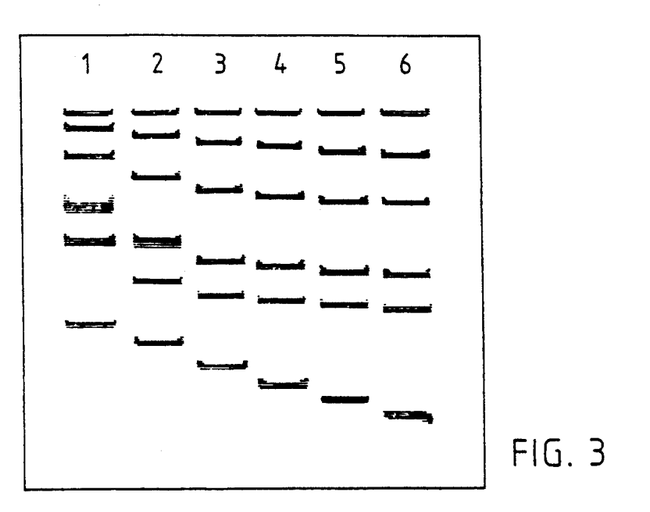
FIG. 3 shows the result of electrophoresis of Pharmacia high molecular weight standard proteins in a polyacrylamide gradient (4 to 24% T, 2.6% C) gel.
Figure 4:
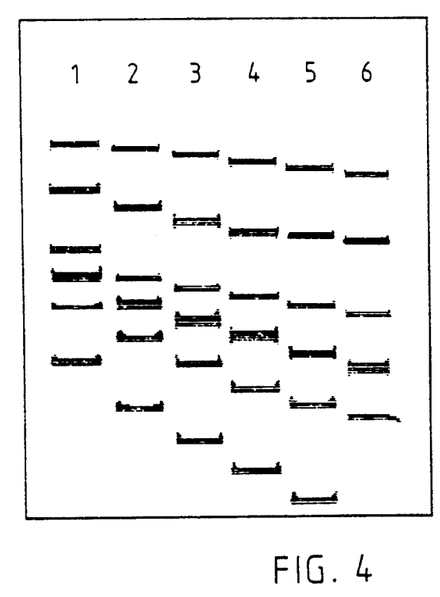
FIG. 4 is similar to FIG. 3, using a poly(NAT+Bis) gradient gel (4 to 24% T, 2.6% C)

Five proteins of different sizes (thyroglobulin (MW 669,000), ferritin (440,000), catalase (232,000), lactate dehydrogenase (140,000), and bovine serum albumin (67,000)) were applied to poly(acrylamide+Bis) and poly(NAT+Bis) gradient gels and run under identical conditions for 400-1400 Vh. The crosslinker concentration (C) was 2.6% in both 4% and 24% monomer solutions. The proteins were run in 0.1M Tris-HCl buffer, pH 9.0, at 200 V for various times: 1, 400 Vh; 2, 600 Vh; 3, 800 Vh; 4, 1000 Vh; 5, 1200 Vh; 6, 1400 Vh. Proteins were stained with Coomassie brilliant blue R-250. The results are shown in FIGS. 3 and 4.

As can be seen, proteins in a poly(acrylamide+Bis) gradient gel occupy the upper, and in a poly(NAT+Bis) gradient the lower, part of the gel. After 1400 Vh, the largest protein (thyroglobulin, MW 690,000) migrated little in the poly(acrylamide+Bis) gel, whereas in the poly(NAT+Bis) gel it passed more than one-third of the gel length. The smallest protein (bovine serum albumin, MW 67,000) had already left the poly(-NAT+Bis) gel in the time it migrated to less than 3/4 of the poly(acrylamide+Bis) gel length.

Figure 5:
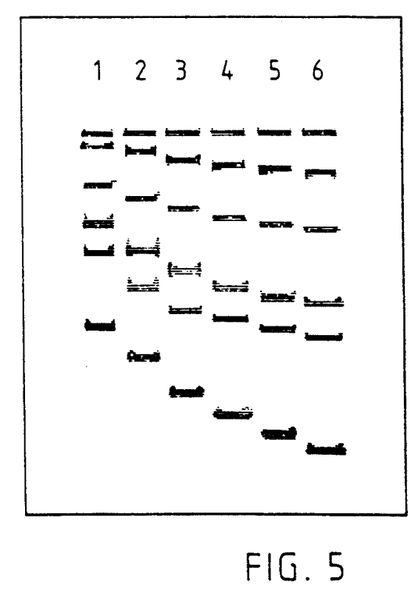
FIG. 5 is similar to FIGS. 3 and 4, using a gradient gel starting with 4% (T) NAT and ending with 24% (T) acrylamide, with an equal concentration (2.6% C) of Bis in both monomer solutions.

Given the similar polymerization kinetics of acrylamide and NAT (FIG. 1), it was thought it should be possible to polymerise a composite gradient gel starting with 4% (T) NAT and ending with 24% (T) acrylamide. Such a gradient gel was obtained and the standard proteins were run in the gel. The results are shown in FIG. 5. In contrast to pure poly(acrylamide+Bis) or pure poly(NAT+Bis) gradient gels (FIGS. 3 and 4), the proteins are now evenly spaced throughout the whole length of the gel. The bands are straight and sharp, indicating that there were no irregularities during copolymerization of the two monomers.

Figure 6:
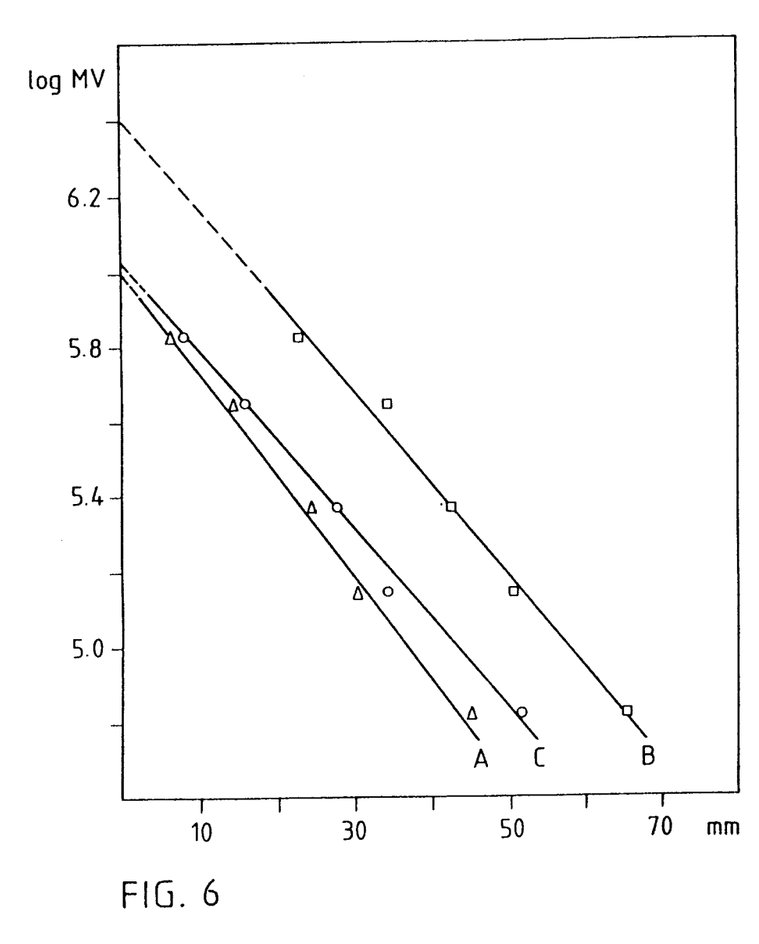
FIG. 6 is a graph of log molecular weight against migration distance (in mm) after 1200 Vh of proteins in the three gels used in FIGS. 3, 4 and 5, where A=-polyacrylamide, B=poly(NAT+Bis)and C=composite poly(NAT+Bis) polyacrylamide gradient gel.

Several mathematical expressions could be used to correlate molecular weight and migration distance of a protein in poly(acrylamide+Bis) gradient gels (reference 20). In order to estimate the exclusion limits of the gels, used for FIGS. 3 to 5, log MW was plotted against migration distance (after 1200 Vh) of proteins in the three gels and straight lines were obtained as shown in FIG. 6. From the rather good fit, it appears that the composite poly(NAT+Bis)-poly(acrylamide+Bis) as well as pure poly(NAT+Bis) gradient gels resolve proteins according to their size. The exclusion limit, estimated by extrapolation to zero migration, of 4-24% poly(NAT+Bis) gradient gels is over $3 \times 10^6$, which is at least threefold higher than the exclusion limit of poly(acrylamide+Bis) gels of the same concentration (FIG. 6). Thus, poly(NAT+Bis) gels appear to be particularly suitable for resolution of large bio-molecules which are normally extensively retarded by the much less porous poly(acrylamide+Bis) gels.

Figure 7:
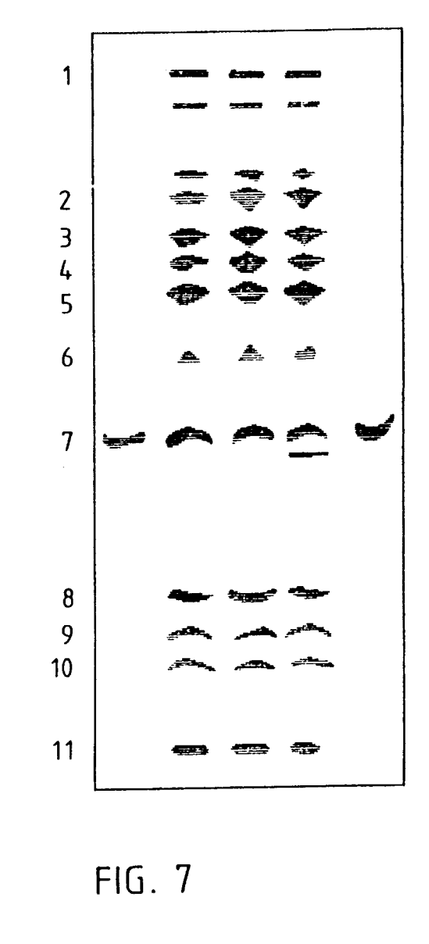
FIG. 7 shows the result of isoelectric focussing of Pharmacia broad pH range standard proteins in a poly(-NAT+Bis) gel (6% T, 3% C).

A typical isoelectric focussing pattern in poly(NAT+Bis) gels (6% T, 3% C) of the broad-range standard proteins is shown in FIG. 7. The anode solution was 0.2M NaOH, and the cathode solution was 1M $H_3PO_4$. The gel contained 2% of 3.5-10 ampholines and was run for 2600 Vh, final voltage 2200 V. The pI markers were: 1, trypsinogen (pI 9.30); 2, lentil lectin basic band (pI 8.65); 3, lentil lectin middle band (pI 8.45); 4, lentil lectin acidic band (pI 8.15); 5, myoglobin basic band (pI 7.35); 6, myoglobin acidic band (pI 6.85); 7, human carbonic anhydrase (pI 6.55); 8, bovine carbonic anhydrase (pI 5.85); 9, betalactoglobulin A (pI 5.20); 10, soybean trypsin inhibitor (pI 4.55); 11, amyloglucosidase (pI 3.50). The standard proteins were run in triplicate, and human carbonic anhydrase was applied to the two outside lanes.

The gel was polymerized onto the plastic sheet (Gel Bond), and it was found that the introduction of the carrier ampholytes after polymerization, as already suggested for poly(acrylamide+Bis) gels Eckersall, P. D., and Conner, J. G. (1984) Anal. Biochem. 138, 52-56, greatly improved the separation. The pH gradient was very much dependent on the concentration of electrode solutions (not shown), and the diluted anode solution, although probably not optimal, gave a much better pH gradient than the 1M NaOH which is usually used with poly(acrylamide+Bis) gels. The focusing for 2000-3000 Vh, at a final voltage of 2300 V, did not cause any adverse effects on the new matrix.

DISCUSSION

Preparation of NAT

The synthesis and polymerization of NAT and several other similar acrylic monomers were described 20 years ago Jedinski, Z., and Paprotny, J. (1966) Ann. Soc. Chim. Pol. 40, 1487-1493; and Eckersall, P. D., and Conner, J. G. (1984) Anal. Biochem. 138, 52-56. The process of the invention as described above is a somewhat modified synthetic route, primarily because the reaction of Tris and acryloyl chloride in acetonitrile Jedinski, Z., and Paprotny, J. (1966) Ann. Soc. Chim. Pol. 40, 1487-1493 was found unsatisfactory for larger scale preparations, due to the low solubility of Tris and NAT in this solvent. The synthesis may conveniently be started with 0.5 mol of Tris, but it should be easily scaled up. NAT has also been synthesized by others Girot, P. and Boschetti, E. (1981), J. Chromatogr. 213, 389-396, but the description of the synthesis is not present in the original reference.

Polymerisation of NAT to make gels

NAT has been used as a principal monomer for the preparation of new, hydrophilic media for chromatography, under the trade name Trisacryl Brown, E., Racois, A., Boschetti, E., and Corgier, M., (1978) J. Chromatogr, 150, 101-110. The functional groups of the ion exchangers were incorporated into the gels by copolymerization of the respective functional monomers with NAT. The first crosslinker was N,N'-diallyl tartardiamide (see Brown et al. supra), but it is not clear whether the same crosslinker is still used commercially since it was recently stated that Trisacryl is produced by copolymerization of NAT and an acrylic crosslinker Saint-Blancard, J., Boschetti, E., Riberon, P., Claudel, P., and Allary, M. (1985) Sci. Tools, 32, 37-40. The Trisacryl gels possess some advantages over gels based on natural polymers (reference 24). However, NAT-based polymers, although stable at low pH, are expected to be more susceptible to alkaline hydrolysis than acrylamide polymers because Tris is better than ammonia as a leaving group from the tetrahedral intermediate formed after the nucleophilic attack of hydroxide ion on the amide carbonyl group. Hydrolysis of the amide bonds would produce carboxyl groups on the matrix which could in turn influence the separation by chromatography or electrophoresis. Since it was not possible to detect any adverse effects in the gels run at pH 9 (FIGS. 4 and 5) or in IEF gels where the anode solution was 0.2 m NaOH, it seems that this potentially deleterious side reaction has no importance under the conditions usually applied in electrophoretic separations.

The exclusion limit of the Trisacryl ion exchangers is over $10^7$ Boschetti, E., (1985) in Affinity Chromatography—A Practical Approach (Dean, P. D. G., Johnson, W. S., and Middle, F. A., Eds.) pp 11-14 IRL Press, Washington, D.C., U.S.A., which makes them an excellent matrix for the separation of large molecules. Trisacryl beads are not transparent, and thus it is likely that the amount of crosslinker used for their preparation was rather high. Opaque, highly cross-linked gels are more porous than the transparent ones because the polymer chains are not evenly distributed throughout the matrix but form solid "knots", leaving large pores in the remaining matrix Righetti, P. G., (1983) in Isoelectric Focusing: Theory, Methodology, and Applications (Work, T. S. and Burdon, R. H. Eds.). Elsevier, Amsterdam and New York. Due to the opacity of the Trisacryl beads (and possibly another crosslinker), it was difficult to predict anything about porosity of the transparent poly(NAT+Bis) gels. By electrophoresis (FIGS. 3 and 4), the higher porosity of poly(NAT+Bis) gels with respect to poly(acrylamide+Bis) has been clearly demonstrated, and this seems to be an intrinsic property of the new monomer. This property is also retained in SDS gels (not shown).

Highly porous matrices are essential in several electrophoretic techniques, and there have been numerous efforts to produce them Bosisio, A. B., Loeherlein, C, Snyder, R. S., and Righetti, P. G., (1980) J. Chromatogr. 189, 317-330 and Baumann, G., and Chrambach, A., (1976) Anal. Biochem. 70, 32-38. In poly(acrylamide+Bis) gels the pores increase as the concentration of Bis rises above 5% Rodbard, D., Levitov, C. and Chrambach, A. (1972), Sep. Sci. 7, 705-723; and Chrambach, A. These gels could be used in electrophoresis, but they are turbid, hydrophobic, and brittle Righetti, P. G., (1983) in Isoelectric Focusing: Theory, Methodology, and Applications (Work, T. S. and Burdon, R. H. Eds.). Elsevier, Amsterdam and New York, which makes handling and visualisation of the bands rather difficult. N,N'-Diallyl tartardiamide was introduced as a new-crosslinker, giving more porous gels when applied at high concentration Baumann, G., and Chrambach, A., (1976) Anal. Biochem. 70, 32–38. However, its use was strongly discouraged after it was found that this crosslinker is in fact an inhibitor of polymerisation, and that the gels crosslinked with it contained very high amounts of unpolymerised material Gelfi, C., and Righetti, P. G., (1981) Electrophoresis 2, 213–219. Other crosslinkers, such as N,N'-(1,2-dihydroxyethylene)bisacrylamide, N,N'-bis-acrylylcystamine, and ethylene diacrylate, although preferable in some respects to Bis Gelfi, C., and Righetti, P. G., (1981) Electrophoresis 2, 213–219, do not produce gels of higher porosity. Thus, it seems that poly(NAT)–Bis gels fulfill the long present need for more porous matrices in electrophoresis.

As discussed above, the first attempts to improve some properties of poly(acrylamide+Bis) gels involved substituting new cross-linkers for Bis. More pronounced effects are obviously obtained by changing the principal monomer, as demonstrated by this invention. Besides higher porosity, which is regarded as the major advantage, poly(NAT+Bis) gels can be dried more easily than poly(acrylamide+CL) gels. Recently, dried poly(acrylamide+CL) gels with immobilised pH gradients for isoelectric focusing became commerically available LKB News Spring (1986) p. 13. Focusing times in the narrow-range immobilized pH gradients are rather long, due to the low mobility of proteins near their isoelectric points. Any sieving exerted by the matrix obviously prolongs the time required by a protein to reach its isoelectric point. Poly(NAT+Bis) gels sieve less than poly(acrylamide+Bis) gels (FIGS. 3 and 4), and therefore they should be advantageous for isoelectric focusing in IPG. Preliminary experiments with an immobilised pH gradient (pH 5.8–6.8) showed that the matrix was completely stable in the strongest electric field tested, i.e., 5000 V over 9-cm distance between the electrodes (not shown). Thus, in contrast to other matrices tested (reference 6), poly(NAT+Bis) gels appear promising for isoelectric focussing in IPG.

REFERENCES

1. Jonhansson, B. G., and Hjerten, S. (1974) Anal. Biochem. 59, 200–213.
2. Bothe, D., Simonis, M., and Dohren, H. V., (1985) Anal. Biochem. 151, 49–54.
3. Campbell, W. P., Wrigley, C. W., and Margolis, J., (1983) Anal. Biochem. 129, 31–36.
4. Lambin, P., (1978) Anal. Biochem. 85, 114–125.
5. Bosisio, A. B., Loeherlein, C., Snyder, R. S., and Righetti, P. G., (1980) J. Chromatogr. 189, 317–330.
6. Righetti, P. G., (1986) Sci. Tools 33, 1–4.
7. Rodbard, D., Levitov, C., and Chrambach, A., (1972) Sep. Sci. 7, 705–723.
8. Chrambach, A., and Rodbard, D., (1971) Science 172, 440–451.
9. Baumann, G., and Chrambach, A., (1976) Anal. Biochem 70, 32–38.
10. Bode, H. J., (1977) Anal. Biochem. 83, 204–210.
11. Bode, H. J., (1977) Anal. Biochem. 83, 364–371.
12. Pino, R. M., and Hart, T. K., (1984) Anal. Biochem. 139, 77–81.
13. Righetti, P. G., (1983) in Isoelectric Focusing: Theory, Methodology and Applications (Work, T. S. and Burdon, R. H. Eds). Elsevier, Amsterdam/New York.
14. Jovin, T. M., (1973) Biochemistry 12, 871–879.
15. Jovin, T. M., (1973) Biochemistry 12, 879–890.
16. Jovin, T. M., (1973) Biochemistry 12, 890–898.
17. Wyckoff, M., Rodbard, D., and Chrambach, A., (1977) Anal. Biochem 78, 459–482.
18. Jedinski, Z., and Paprotny, J., (1966) Ann. Soc. Chim. Pol. 40, 1487–1493
19. Gelfi, C., and Righetti, P. G., (1981) Electrophoresis 2, 213–219.
20. Rothe, G. M., and Purkhanbaba, H., (1982) Electrophoresis 3, 33–42.
21. Eckersall, P. D., and Conner, J. G., (1984) Anal. Biochem. 138, 52–56.
22. Jedinski, Z., and Paprotny, J., (1967) J Polym. Sci. 5, 2957–2960.
23. Girot, P., and Boschetti, E., (1981) J. Chromatogr. 213, 389–396.
24. Brown, E., Racois, A., Boschetti, E., and Corgier, M., (1978) J. Chromatogr. 150. 101–110.
25. Saint-Blancard, J., Boschetti, E., Riberon, P., Claudel, P., Girot, P., and Allary, M., (1985) Sci. Tools 32, 37–40.
26. Boschetti, E., (1985) in Affinity Chromatography - A Practical Approach (Dean, P. D. G., Johnson, W. S., and Middle, F. A., Eds.) pp 11–14 IRL Press, Washington D.C.
27. LKB News Spring (1986) p. 13.
28. Kozulic, B., Mosback, K., and Pietrzak, M. (1988) Anal Biochem 170, 478–484.

What is claimed is:

1. A gel which is sufficiently water-insoluble and sufficiently transparent to be useful in electrophoresis, and which has an insufficient amount of charged groups to affect the gel in an electric field;

wherein said gel comprises about 4 to 24% of a copolymer which does not contain charged groups in an amount sufficient to affect a gel made therefrom when said gel is placed in an electric field, which copolymer comprises monomer and crosslinker;

wherein said monomer comprises N-acryloyl-tris(hydroxymethyl) aminoethane (NAT);

wherein said crosslinker comprises N, N'-methylene-bis-acrylamide (BIS);

wherein said copolymer contains an amount sufficient to crosslink said monomer, up to 5% based on the sum of the weight of monomer and crosslinker, of crosslinker; and wherein said copolymer is made by co-polymerization of said monomer and said crosslinker in the absence of carrier ampholytes.

2. The method of separating molecules in an electric field in contact with a separation medium which comprises conducting said separation in the effective presence of a separation medium comprising a gel which is sufficiently water insoluble and sufficiently transparent to be useful in electrophoresis, and which has an insufficient amount of charged groups to affect the gel in an electric field;

wherein said gel comprises about 4 to 24% of a copolymer which does not contain charged groups in an amount sufficient to affect a gel made therefrom when said gel is placed in an electric field, which copolymer comprises monomer and crosslinker;

wherein said monomer comprises N-acryloyl-tris(hydroxymethyl) aminoethane (NAT);

wherein said crosslinker comprises N,N'-methylene-bis-acrylamide (BIS);

wherein said copolymer contains an amount sufficient to crosslink said monomer, up to 5% based on the sum of the weight of monomer and crosslinker, of crosslinker; and wherein said copolymer is made by co-polymerization of said monomer and said crosslinker in the absence of carrier ampholytes.

3. A method of claim 2 wherein the gel has been dried and reswollen.

4. A method of claim 2 wherein the gel is prepared in situ on the support.

5. A method of claim 2 wherein the gel is in the form of a gradient gel.

6. A method of claim 2 wherein the molecules comprise proteins and the separation is conducted under either nondenaturing or denaturing conditions.

7. A method of claim 2 wherein the molecules comprise nucleic acids or polynucleotides and the separation is conducted under nondenaturing or denaturing conditions.

8. A method of claim 2 wherein the molecules have intrinsic charged groups.

9. A method of claim 2 wherein said molecules have charges formed by derivatisation of uncharged molecules.

10. A method of claim 2 conducted in a continuous or a discontinuous buffer system.

11. A method of claim 2 conducted under discontinuities in time and/or electric field.

12. A method of claim 2 wherein proteins are separated according to their isoelectric point in a pH gradient formed by carrier ampholytes, the ampholytes being introduced in the gel after its polymerization.

13. A method of claim 2 wherein proteins are separated according to their isoelectric points in an immobilized pH gradient.

14. A method a separating molecules in an electric field comprising effectively contacting a mixture of said molecules with a separation medium while being subjected to an electric field sufficient to cause the separation of said molecules in said separation medium;

wherein said separation medium comprises a gel which is sufficiently water insoluble and sufficiently transparent to be useful in electrophoresis, and which has an insufficient amount of charged groups to affect the gel in an electric field;

wherein said gel comprises about 4 to 24% of a polymer which does not contain any charged groups in an amount sufficient to affect said gel in an electric field, which polymer comprises;

N-acryloyl-tris-(hydroxymethyl) aminoethane (NAT) monomer, and an additional material which is polymerizable with said monomer; and wherein said polymer is made by polymerization of said monomer and said additional material in the absence of added materials which contain a sufficient amount of charged groups to affect a gel made from said polymer when said gel is placed in an electric field.

15. A method of claim 14 wherein said additional gel material comprises a cross-linker contains two or more ethylenic double bonds and is present in the weight ratio of CL to (NAT+CL) from 0.0001 to 0.5.

16. A method of claim 14 wherein said additional material comprises acrylamide as an additional monomer.

17. A method of claim 16 wherein said additional monomer comprises acrylamide at a concentration of 0.5 to 25% (w/v).

18. A method of claim 14 wherein said gel material is admixed with at least one member selected from the group consisting of acrylamide and agarose, at the concentration of 0.1 to 6% (w/v), having an insufficient charge to affect the gel in an electric field.

19. A method of claim 14 wherein the gel has been dried and reswollen.

20. A method of claim 24 wherein the gel is fixed to a solid support.

21. A method of claim 14 wherein the gel was prepared in situ on the support.

22. A method of claim 14 wherein the gel is in the form of a gradient gel.

23. A method of claim 14 wherein the molecules being separated by electrophoresis comprise proteins and the separation is conducted under nondenaturing or denaturing conditions.

24. A method of claim 14 wherein the molecules being separated by electrophoresis comprise nucleic acids or polynucleotides and the separation is conducted under nondenaturing or denaturing conditions.

25. A method of claim 14 wherein the molecules being separated by electrophoresis have intrinsic charged groups therein.

26. A method of claim 25 wherein said molecules have charges formed by derivatisation of uncharged molecules.

27. A method of claim 14 conducted a continuous or a discontinuous buffer system.

28. A method of claim 14 conducted under discontinuities in time and/or electric field.

29. A method of claim 14 wherein said molecules being separated by electrophoresis comprise proteins, and wherein said proteins are separated according to their isoelectric point in a pH gradient formed by carrier ampholytes, the ampholytes being introduced into combination with the gel after its polymerization.

30. A method of claim 14 wherein said molecules being separated by electrophoresis comprise proteins, and wherein said proteins are separated according to their isoelectric points in an immobilized pH gradient.

31. A method as claimed in claim 14, wherein said additional material comprises a cross-linker having at least two ethylenic double bonds, and wherein said cross-linker is present in said polymer in an amount sufficient to cause crosslinking of said (NAT) up to a weight proportion of about 5%, based upon the total weight of said (NAT) and said cross-linker.

32. The method of as claimed in claim 14 wherein said additional material comprises a crosslinker, comprising N,N'-methylene-bis-acrylamide (BIS), and at least one additional monomer which is polymerizable with said (NAT) and has an insufficient amount of charged groups to affect said gel in an electric field.

33. The method as claimed in claim 32 wherein said additional monomer comprises acrylamide.

34. The method as claimed in claim 14 wherein said additional material is at least one member selected from the group consisting of N,N'-methylene-bis-acrylamide (BIS), N,N'-bis-acrylyl-cystamine, and ethylenediacrylate.

* * * * *